(12) United States Patent
Schiffer et al.

(10) Patent No.: US 8,293,279 B2
(45) Date of Patent: Oct. 23, 2012

(54) PH-REGULATED POLYAMIDE POWDER FOR COSMETIC APPLICATIONS

(75) Inventors: Thomas Schiffer, Bergisch Gladbach (DE); Holger Renners, Velen-Ramsdorf (DE); Wolfgang Christoph, Marl (DE); Franz-Erich Baumann, Duelmen (DE); Joachim Muegge, Haltern (DE)

(73) Assignee: Evonik Degussa GmbH, Essen (DE)

( * ) Notice: Subject to any disclaimer, the term of this patent is extended or adjusted under 35 U.S.C. 154(b) by 717 days.

(21) Appl. No.: 12/173,382

(22) Filed: Jul. 15, 2008

(65) Prior Publication Data

US 2008/0279904 A1     Nov. 13, 2008

Related U.S. Application Data

(63) Continuation of application No. 10/317,122, filed on Dec. 12, 2002, now abandoned.

(30) Foreign Application Priority Data

Dec. 12, 2001   (DE) .................................. 101 61 038

(51) Int. Cl.
*A61K 9/16* (2006.01)
*A61K 9/18* (2006.01)

(52) U.S. Cl. .......... 424/497; 424/69; 424/401; 424/501; 424/489

(58) Field of Classification Search .................. 424/489, 424/501, 69, 401
See application file for complete search history.

(56) References Cited

U.S. PATENT DOCUMENTS

| | | | |
|---|---|---|---|
| 3,679,638 A | 7/1972 | Korsgen et al. |
| 4,069,184 A | 1/1978 | Ferraro et al. |
| 4,194,993 A | 3/1980 | Deal, III |
| 4,831,061 A | 5/1989 | Hilaire et al. |
| 5,405,936 A | 4/1995 | Mumcu et al. |
| 5,668,242 A | 9/1997 | Simon et al. |
| 5,928,652 A | 7/1999 | Bodelin-LeComte |
| 5,932,687 A | 8/1999 | Baumann et al. |
| 6,060,550 A | 5/2000 | Simon et al. |
| 6,149,836 A | 11/2000 | Mumcu et al. |
| 6,300,413 B1 | 10/2001 | Simon et al. |
| 6,316,537 B1 | 11/2001 | Baumann et al. |
| 6,335,101 B1 | 1/2002 | Haeger et al. |
| 6,348,532 B1 | 2/2002 | Mayer |
| 6,403,851 B1 | 6/2002 | Wilczok et al. |
| 6,407,304 B2 | 6/2002 | Schiffer et al. |
| 6,444,855 B1 | 9/2002 | Esser et al. |
| 6,462,235 B1 | 10/2002 | Thiele et al. |
| 6,566,555 B2 | 5/2003 | Thiele et al. |
| 6,579,581 B2 | 6/2003 | Bartz et al. |
| 6,589,606 B2 | 7/2003 | Waterkamp et al. |
| 6,610,864 B2 | 8/2003 | Krebs et al. |
| 6,620,970 B2 | 9/2003 | Schiffer et al. |
| 6,639,108 B2 | 10/2003 | Schiffer et al. |
| 6,656,997 B2 | 12/2003 | Baumann et al. |
| 6,664,423 B2 | 12/2003 | Herwig et al. |
| 6,677,015 B2 | 1/2004 | Himmelmann et al. |
| 6,766,091 B2 | 7/2004 | Beuth et al. |
| 6,784,227 B2 | 8/2004 | Simon et al. |
| 6,852,893 B2 | 2/2005 | Kuehnie et al. |
| 6,884,485 B2 | 4/2005 | Baumann et al. |
| 2003/0124281 A1 | 7/2003 | Ries et al. |
| 2003/0191223 A1 | 10/2003 | Waterkamp et al. |
| 2004/0086735 A1 | 5/2004 | Monsheimer et al. |
| 2004/0097636 A1 | 5/2004 | Baumann et al. |
| 2004/0102539 A1 | 5/2004 | Monsheimer et al. |
| 2004/0106691 A1 | 6/2004 | Monsheimer et al. |
| 2004/0137228 A1 | 7/2004 | Monsheimer et al. |
| 2004/0138363 A1 | 7/2004 | Baumann et al. |
| 2004/0140668 A1 | 7/2004 | Monsheimer et al. |
| 2004/0180980 A1 | 9/2004 | Petter et al. |
| 2004/0206443 A1 | 10/2004 | Monsheimer et al. |
| 2004/0232583 A1 | 11/2004 | Monsheimer et al. |
| 2005/0014842 A1 | 1/2005 | Baumann et al. |
| 2005/0027047 A1 | 2/2005 | Monsheimer et al. |
| 2005/0027050 A1 | 2/2005 | Monsheimer et al. |
| 2005/0038201 A1 | 2/2005 | Wursche et al. |

FOREIGN PATENT DOCUMENTS

FR     2 365 597     4/1978

OTHER PUBLICATIONS

Flick, E., Cosmetic and Toiletry Formulations, 1999, Noyes Publications/William Andrew Publishing, LLC, ($2^{nd}$ et), vol. 7, p. 89.
Brydson, J., Plastics Materials, 1999, Butterworth-Heinemann, $7^{th}$ ed., p. 528.
Braun, D. et al., Rheology Modifiers handbook, 2000, William Andrew Publishing, p. 345.

*Primary Examiner* — Gina C Yu
(74) *Attorney, Agent, or Firm* — Oblon, Spivak, McClelland, Maier & Neustadt, L.L.P.

(57) ABSTRACT

The present invention relates to polyamide powders suitable for cosmetic applications are described which have a pH of 4.0 to 7.0, cosmetic compositions containing the polyamide powders and processes of making the same.

14 Claims, No Drawings

PH-REGULATED POLYAMIDE POWDER FOR COSMETIC APPLICATIONS

CROSS-REFERENCE TO RELATED APPLICATIONS

This application is a continuation of U.S. Ser. No. 10/317,122 filed Dec. 12, 2002, abandoned and claims the benefit of DE 101 61 038.6 filed Dec. 12, 2001.

FIELD OF THE INVENTION

The invention relates to a polyamide powder suitable for cosmetic applications which has a defined pH in aqueous suspension, and to the preparation thereof.

BACKGROUND OF THE INVENTION

Polyamide fine powders are used in numerous cosmetic products, such as, for example, in lipsticks, make-ups, powders and creams. They generally comprise fine powders based on polyamide 11 and/or polyamide 12, and also polyamide 6 and PA6/12 copolymers having an average particle diameter of from 5 to 30 µm. Polyamide powders with a larger average particle diameter of up to 400 µm are used, inter alia, in shower gels to achieve a peeling effect.

Since cosmetics are in direct contact with the human skin, high dermatological requirements are placed on their contents with regard to purity and their skin compatibility. Polyamide fine powders used hitherto already satisfy the high purity requirements. The precipitation process and anionic polymerization, in particular, are known for preparing such cosmetic powders based on polyamide. Other specific processes preparing cosmetic powders, as disclosed in JP 04050232 and JP 05070598 (both Daicel-Hüls) and JP 05025019 (Kao Corp.), have not achieved industrial importance.

However, powders from both processes frequently have, as a result of their respective preparation process, a pH which is outside the range which is regarded by dermatologists as the optimum pH range for the acid protective mantle of the skin. A pH which is either too acidic or too basic can lead to skin irritations. In particular, a basic pH also causes the skin to dry out. As a result, the skin becomes brittle and its elasticity decreases. In addition, under stress, cracks and small skin injuries may rapidly result.

The precipitation process described in DE 29 06 647 B1, provides a suitable polyamide-12 granulate, which is completely dissolved in hot alcohol under pressure. Upon cooling fine particles crystallize out, the growth of which is controlled by the cooling rate and optionally also by small amounts of phosphorus-containing acids. When crystallization of the polyamide particles is complete, the alcohol is stripped off. Small amounts of phosphorus-containing acids (e.g. hypophosphorus acid, phosphorus acid and/or phosphoric acid), however, remain incorporated within the polyamide, as a result of which these fine powders tend to have a slightly acidic reaction in aqueous suspension, the pH being 4-6 depending on the carboxyl end-group excess and phosphoric acid content, and in extreme cases may even be below pH 4. These pH values do not correspond to the market requirements in certain fields.

During anionic solution polymerization, an anionically activated polymerization of monomeric lactam, preferably laurolactam, takes place in higher-boiling paraffins (140 to 170° C.). Strongly basic catalysts are used for this purpose, as a result of which such fine powders usually have a slightly basic/alkaline reaction despite repeated washing. The pH values of such powders are between 7 and 8.5.

The fine powders obtained from both processes have a round particle shape. Powders from the two processes are usually protection-screened and/or sifted and may optionally be subsequently ground to increase the proportion of fines.

Most cosmetic preparations generally comprise only between 0.1 and 10% by weight of polyamide fine powder. Depending on the field of use, the remainder consists of a variety of oils, fats, emulsifiers, stabilizers, and also dyes and aroma substances. They usually comprise a sufficiently large buffer system in order to produce a cosmetic application with a skin-friendly pH.

However, for some time there has also been an explicit desire on the part of the cosmetics industry for pH-regulated polyamide powders.

Surprisingly, it has now been found that the pH of polyamide powders as described in the claims, in particular precipitated powders, polyamide powders which have been prepared according to the precipitation process, can be well regulated if they are equipped with a special buffer system. This buffer system is based here preferably on naturally occurring acids and their corresponding salts. In addition, the slightly basic polyamide powder can also be buffered using the process according to the invention.

SUMMARY OF THE INVENTION

In one embodiment of the invention, a polyamide powder with a pH which is in the range of the natural acid protective mantle of the skin. Preferably, this pH is from 4 to 7.

This polyamide powder is achieved by adding a buffer system to the polyamide powder.

Another embodiment of the invention is a cosmetic composition containing the polyamide powder with the specified pH and a carrier

DETAILED DESCRIPTION OF THE INVENTION

Suitable polyamide powders are, in particular, powders which have polyamide 11 and/or polyamide 12. Particular preference is given to a polyamide 12 precipitated powder with porous surfaces, as arise in accordance with DE 29 06 647 B1.

Preferably, the polyamide powder according to the invention has an average particle size diameter ($d_{50}$) of from 1 to 400 µm, preferably 5 to 100, particularly preferably 5 to 60.

As used herein "buffer system" is understood to mean the combinations of weak organic and/or mineral acids and their corresponding salts.

As used herein "naturally occurring acids" are understood to mean organic and/or mineral compounds which are either formed in the human body itself or are frequently taken in by humans, for example with food or via the skin, without resulting, as far as is known, in any damage to health. It is also important here that the compounds can be degraded completely by the human organism and that, as far as is known, neither the compounds themselves which have been taken in, nor their metabolites, lead to health damage.

In one embodiment, the buffer system is based on natural organic and/or inorganic acids, i.e. acids which occur in the human body, and salts thereof. Examples of which are phosphate buffer and/or citrate buffer.

Salts which can be used include all bases corresponding to the abovementioned acids. For this purpose, use is usually made of physiologically safe alkali metal and alkaline earth metal salts, and ammonium salts, although other cations are also possible.

For the purposes of the invention, the term "acid" also covers the corresponding hydrogen salts of polybasic acids, for example sodium dihydrogenphosphate or disodium hydrogencitrate.

According to the current level of understanding for applications to the skin, a pH of from 4 to 7 is generally recommended by dermatologists in order to avoid irritations or drying out of the skin. Particular preference is given to a pH range of from 4.5 to 6.5, and more particularly from 5.0 to 6.0.

A concrete "optimum" pH of the skin cannot generally be given. It differs from person to person, possibly due to the respective skin type. It also depends on the sex and age of the person in question (see, inter alia, Römpp Chemielexikon, 9th edition, p. 1743).

A prerequisite for the use of the respective acid and its corresponding bases is that the system resulting therefrom forms a buffer of adequate capacity in the abovementioned pH range. A decisive parameter when choosing the acid is the pKa value. From this, the respective pH of an aqueous solution can be determined via the Henderson-Hasselbalch equation:

$$pH = pKa - \log\{c(HA)/c(A^-)\}$$

where HA=acid and $A^-$=corresponding base

In the case of polybasic acids, the corresponding mono- or dihydrogen salts are used in place of the free acid. A few pKa values at 25° C. of suitable tribasic acids for buffer systems are given as nonlimiting examples below. Here, the pKa values suitable for the cosmetic powders are in bold font:
Citric Acid:
$pKa_1$=3.128, $pKa_2$=4.761, $pKa_3$=6.396
Phosphoric Acid:
$pKa_1$=2.15, $pKa_2$=7.09, $pKa_3$=12.32

For citric acid, a suitable buffer is the $pKa_3$ value, i.e., for example, the disodium hydrogencitrate/trisodium citrate system. For phosphoric acid, it is the $pKa_2$ value, for example in the form of the sodium dihydrogenphosphate/disodium hydrogenphosphate system.

The content of buffer system in the cosmetic powder should be kept as low as possible. The cosmetic properties of the polyamide powder should also be influenced as little as possible by the content of buffer system. At the same time, however, an adequate buffer capacity should be achieved in order to be able to maintain the desired pH in the cosmetic powder.

When preparing the buffer mixture, it is advantageous to include the content of acid and base functions in the polyamide. This refers both to the carboxyl and amino end-groups of the polyamide chains and also to acidic or basic added substances which have functioned during the polymerization as catalyst (e.g. phosphorus-containing acid) or as regulator (e.g. dodecanedioic acid).

The content of acid and amino functions in the polyamide can be readily quantified, for example, by titrimetric methods. These are generally known and can be found, for example, in Kunststoff-Handbuch, volume 3, 4 "Polyamide", Hanser Verlag, Munich.

If there is an excess of acidic functional groups in the polyamide, then the free acid in the buffer component can be reduced or in some cases omitted entirely. In the case of an excess of basic functions in the polyamide, the corresponding base in the buffer can be reduced accordingly.

The buffer system, comprising acid and corresponding base, is chosen so that as a rule there are 0.001 to 10 parts of the buffer per 100 parts of polyamide, preferred limits being 0.01 to 2 parts of the buffer system per 100 parts of polyamide, and more preferably 0.1 to 1 parts of the buffer system per 100 parts of polyamide.

The buffer system can be incorporated into the polyamide according to the invention via various processes.

In the dry blend, buffer system and polyamide powder are mixed dry and intimately. A prerequisite for this is that the ground buffer system does not have a significantly larger average particle diameter than the respective polyamide fine powder. Preferably, the buffer system is first ground as fine as possible in the dry state, so that the average particle diameter is significantly lower than the average diameter of the polyamide particle. The buffer system can then penetrate upon mixing into the pores of the polyamide particle. For this, porous polyamide precipitated powders are particularly suitable.

To prepare polyamide fine powders with an average particle diameter $d_{50}$ of less than 20 μm, it is advisable that polyamide powder and the buffer system are firstly mixed together and then ground and sifted in a common step to the desired particle size.

Alternatively to dry blending, the buffer system can also attach to the polyamide particles in solution. This process can be used for all polyamide powders. In the case of a precipitated powder, such as VESTOSINT, however, this process is particularly advantageous. This step can in this case also be integrated in a combined mixer/dryer directly in the precipitation process. Time can be saved if the drying of the polyamide powder from the precipitation process and incorporation of the buffer system take place in the same container, which can also reducing processing to one step.

The buffer system, dissolved in a solvent, can also be sprayed onto the polyamide particles. Suitable solvents are include water and/or aqueous-alcoholic solutions. The solvent is then stripped off completely at elevated temperatures in the mixer, and/or under vacuum.

The increased temperatures in the mixer have the effect that in this process the buffer system is present in very finely and uniformly dispersed form on the polyamide particle, and the free carboxyl and amino end-groups in the polyamide have already chemically reacted and are completely buffered.

The preparation of the cosmetic powders according to the invention can be carried out as dry blend. For example, polyamide powder and buffer system are used as solids. The buffer system can either be ground on its own and then mixed with the polyamide fine powder, or the buffer system and polyamide powder are mixed together and then ground and sifted together.

A further preparation process includes adding a buffer solution to the polyamide powder and then freeing it together with the polyamide from the solvent. This results in a particularly uniform distribution of the buffer system in the polyamide particle, which is particularly suitable for porous precipitated powders. The process is preferably integrated into the drying step of the precipitation process, but can also be carried out subsequently on a dry fine powder.

The pH of the polyamide powder is determined in each case in suspension of 1 g of powder in 100 ml of distilled water. After stirring for 24 h, the incorporated acids and/or bases have dissolved out of the polyamide. The pH is determined using a calibrated pH electrode. Results are summarized in table 1.

The present invention also provides cosmetic compositions containing the polyamide powders having the pH as described herein. These cosmetic compositions will also include one or more cosmetically acceptable carriers, fragrances, pigments, fillers, and other common ingredients used in cosmetics, such as, emulsifiers, polymers, surfactants, conditioning agents, humectants, sunscreens, etc. These and other suitable cosmetic ingredients are known in the art, and are described, for example, in International Cosmetic, Toiletries, and Fragrance Association Handbook, 8th Edition (2000).

Having generally described this invention, a further understanding can be obtained by reference to certain specific examples which are provided herein for purposes of illustration only, and are not intended to be limiting unless otherwise specified.

EXAMPLES

Example 1

Preparation of the Polyamide Fine Powders, Precipitation Process Corresponding to DE 29 06 647 B1

60 kg of unregulated PA12 prepared by hydrolytic polymerization of laurolactam and having a relative solution viscosity $\eta_{rel}$ of 1.61 (in acidified m-cresol) and an end-group content of 72 mmol/kg of COOH and 68 mmol/kg of $NH_2$ are brought, with 375 l of ethanol, denatured with 2-butanone and 1% water content, in a stirred vessel to 145° C. and left for 1 hour at this temperature with stirring (paddle stirrer).

The jacket temperature is then reduced to 124° C., 60 g of phosphoric acid are added as crystallization auxiliary and, with continuous removal of the ethanol by distillation, the internal temperature is brought to 125° C. with stirring at a cooling rate of 25 K/h. From now on, at the same cooling rate, the jacket temperature is maintained at 2 K-3 K below the internal temperature until, at 109° C., precipitation, recognizable from the evolution of heat, starts. Distilling off ethanol ensures that the internal temperature does not exceed 109.5° C. After about 20 minutes the internal temperature drops, which indicates the end of the precipitation. Further distillation and cooling via the jacket brings the temperature of the suspension to 45° C. and the suspension is then transferred to a dryer. The ethanol is distilled off at 70° C./400 mbar, and the residue is then after-dried at 20 mbar/85° C. for 3 hours.

The desired fine fractions are separated off by repeated screening and sifting corresponding to their average particle diameter.

Example 2

Preparation of the Polyamide Fine Powders, Precipitation Process, Anionic Polymerization in Accordance with EP 0 192 515

A round flask is charged, under protective gas (argon), with 300 ml of dry decalin. At elevated temperature (80° C.), 80 g of laurolactam and 3 g of N,N'-ethylenediaminebisoleamide are dissolved with stirring (600 rpm), and 400 mg of silicon dioxide are added as nucleating agent. Traces of water are removed from the reaction mixture by distilling off about 10% of the solvent under reduced pressure at 120 to 130° C. Then, under protective gas and at about 110° C. and atmospheric pressure, 175 mg of sodium hydride are added (Fluka, about 60% strength in oil). The reaction mixture is kept for a further 30 minutes at 110° C., then cooled at 0.2 K/min to 100° C. Over the course of 2 h 4.5 g of stearyl isocyanate are added via a dosing pump. After cooling the mixture to 90° C., the precipitate is separated off as a fine white powder. It is washed with 100 ml of ethanol at room temperature and dried in a vacuum drying cabinet at 200 mbar, 60° C.

Example 3

Comparative Example 1.0 g of the polyamide 12 precipitated powder from example 1 with an average particle size $d_{50}$=20 µm is suspended in 100 ml of distilled water and stirred for 24 h. The pH is measured using a digital pH meter (Schott CG 843). The results are summarized in table 1.

Example 4

Comparative Example

Analogously to example 3, 1.0 g of anionically polymerized polyamide 12 powder from example 2 is suspended in 100 ml of distilled water and stirred for 24 h. The pH is measured using a digital pH meter (Schott CG 843). The results are summarized in table 1.

Example 5

0.1 g of finely ground and sifted trisodium citrate dihydrate ($d_{50} \leq 10$ µm) is added to 100 g of the polyamide 12 precipitated powder from example 1 with an average particle size $d_{50}$=20 µm, and the mixture is mixed in the dry blend on a Diosna mixer for 3 minutes at 500 rpm. 1.0 g of the mixture is suspended in 100 ml of distilled water and stirred for 24 h. The pH is measured using a digital pH meter (Schott CG 843). The results are summarized in table 1.

Example 6

The experiment of example 5 is repeated with 0.5 g of finely ground and sifted trisodium citrate dihydrate ($d_{50} \leq 10$ µm). The results are summarized in table 1.

Example 7

The experiment of example 5 is repeated with 1.2 g of finely ground and sifted trisodium citrate dihydrate ($d_{50} \leq 10$ µm) and 0.5 g of finely ground and sifted disodium hydrogencitrate sesquihydrate ($d_{50} \leq 10$ µm). The results are summarized in table 1.

Example 8

The experiment of example 5 is repeated with 0.5 g of finely ground and sifted trisodium citrate dihydrate ($d_{50} \leq 10$ µm) and 1.2 g of finely ground and sifted disodium hydrogencitrate sesquihydrate ($d_{50} \leq 10$ µm). The results are summarized in table 1.

Example 9

The experiment of example 5 is repeated with 2.0 g of finely ground and sifted trisodium citrate dihydrate ($d_{50} \leq 10$ µm). The results are summarized in table 1.

Example 10

60 kg of precipitated powder were prepared according to the experiment of example 1 and predried in a mixer at 70° C./400 mbar for 30 min. The still-damp powder is sprayed, with stirring, with a solution of 960 g of trisodium citrate dihydrate and 5 l of distilled water. The solvent is distilled off at 70° C./400 mbar and the residue is then dried at 20 mbar/85° C. for 3 hours.

The desired fine fractions are separated off according to their average particle diameter by repeated screening and sifting.

Example 11

1.00 g of the polyamide 12 precipitated powder from example 10 with an average particle size $d_{50}=20$ µm is suspended in 100 ml of distilled water and stirred for 24 h. The pH is measured using a digital pH meter (Schott CG 843). The results are summarized in table 1.

Example 12

60 kg of precipitated powder are prepared according to the experiment of example 1 and predried in a mixer at 70° C./400 mbar for 30 min. The still-damp powder is sprayed, with stirring, with a solution of 720 g of trisodium citrate dihydrate, 300 g of disodium hydrogencitrate sesquihydrate and 5 l of distilled water. The solvents are distilled off at 70° C./400 mbar and the residue is then dried at 20 mbar/85° C. for 3 hours.

The desired fine fractions are separated off according to their average particle diameter by repeated screening and sifting.

Example 13

1.00 g of the polyamide 12 precipitated powder from example 12 with an average particle size $d_{50}=20$ µm is suspended in 100 ml of distilled water and stirred for 24 h. The pH is measured using a digital pH meter (Schott CG 843). The results are summarized in table 1.

TABLE 1

| Example | Trisodium citrate dihydrate [g/100 g] | Disodium hydrogencitrate* sesquihydrate [g/100 g] | pH [after 24 h] |
| --- | --- | --- | --- |
| 3 | — | — | 4.6 |
| 4 | — | — | 8.4 |
| 5 | 0.1 | — | 5.0 |
| 6 | 0.5 | — | 6.2 |
| 7 | 1.2 | 0.5 | 6.4 |
| 8 | 0.5 | 1.2 | 5.9 |
| 9 | 2.0 | — | 7.2 |
| 11 | 1.6 | — | 6.3 |
| 13 | 1.2 | 0.5 | 6.2 |

Obviously, numerous modifications and variations on the present invention are possible in light of the above teachings. It is therefore to be understood that within the scope of the appended claims, the invention may be practiced otherwise than as specifically described herein.

The present invention claims priority to DE 101 61 038.6, which was filed on Dec. 12, 2001, and the contents of which are incorporated herein by reference.

The invention claimed is:

1. A method of making a fine polyamide powder suitable for a cosmetic application, the method comprising adding from 0.01 to 2 parts of a buffer system per 100 parts of polyamide, wherein the buffer system comprises at least one of a natural organic acid, a natural mineral acid, and a corresponding salt thereof, and polyamide powder in a manner to yield a uniform distribution of the buffer system with the polyamide powder,
wherein the resulting fine polyamide powder is suitable for a cosmetic application and has a pH of from 4.0 to 7.0 which is the pH a suspension of 100 ml of water and 1 g of the fine polyamine powder measured after stirring the suspension for 24 hours,
wherein the buffer system is dry and is mixed with a dry blend of the polyamide powder, and
wherein the fine polyamide powder has an average particle diameter $d_{50}$ of from 1 to 400 µm.

2. The method as claimed in claim 1, wherein the polyamide powder has a pH of from 4.5 to 6.5.

3. The method as claimed in claim 1, wherein the buffer system comprises at least one of a citrate buffer and a phosphate buffer.

4. The method as claimed in claim 1, wherein the polyamide powder is at least one polyamide selected from the group consisting of polyamide 11 and polyamide 12.

5. The method as claimed in claim 1, wherein the polyamide powder is obtained by a precipitation process or by an anionic solution polymerization process.

6. The method as claimed in claim 1, comprising adding from 0.1 to 1 parts of the buffer system per 100 parts of the polyamide.

7. The method as claimed in claim 1, further comprising grinding the buffer system in the dry state, thereby yielding fine buffer system particles having an average particle diameter smaller than an average particle diameter of the polyamide powder, wherein the ground buffer system penetrates into pores of the polyamide powder particles upon mixing.

8. The method as claimed in claim 1, wherein the polyamide powder is porous polyamide precipitated powder.

9. The method as claimed in claim 1, further comprising grinding a mixture of the buffer system and the polyamide powder in the dry state to the desired particle size, wherein the average particle diameter $d_{50}$ of the resulting fine polyamide powder less than 20 µm.

10. The method as claimed in claim 1, further comprising separately grinding the buffer system and the polyamide powder in the dry state to the desired average particle size prior to mixing.

11. The method as claimed in claim 1, wherein the average particle diameter $d_{50}$ of the resulting fine polyamide powder is from 5 to 100 µm.

12. The method as claimed in claim 1, wherein the average particle diameter $d_{50}$ of the resulting fine polyamide powder is from 5 to 60 µm.

13. The method as claimed in claim 1, wherein the pH is from 5 to 6.

14. The method as claimed in claim 1, further comprising grinding the buffer system, wherein an average particle diameter $d_{50}$ of the ground buffer system is not greater than 10 µm.

* * * * *